US012721719B2

(12) United States Patent
Scarpone

(10) Patent No.: US 12,721,719 B2
(45) Date of Patent: Sep. 1, 2026

(54) METHODS FOR ATTACHING TENDONS AND/OR LIGAMENTS TO BONE AND/OR CARTILAGE

(71) Applicant: Michael A. Scarpone, Bloomingdale, OH (US)

(72) Inventor: Michael A. Scarpone, Bloomingdale, OH (US)

(73) Assignee: Michael A. Scarpone, Bloomingdale, OH (US)

( * ) Notice: Subject to any disclaimer, the term of this patent is extended or adjusted under 35 U.S.C. 154(b) by 401 days.

(21) Appl. No.: 18/529,559

(22) Filed: Dec. 5, 2023

(65) Prior Publication Data

US 2024/0180689 A1 Jun. 6, 2024

Related U.S. Application Data

(60) Provisional application No. 63/386,251, filed on Dec. 6, 2022.

(51) Int. Cl.

*A61F 2/08* (2006.01)
*A61L 27/38* (2006.01)
*A61L 27/50* (2006.01)

(52) U.S. Cl.

CPC .......... *A61F 2/0805* (2013.01); *A61F 2/0811* (2013.01); *A61L 27/386* (2013.01); *A61L 27/50* (2013.01)

(58) Field of Classification Search

CPC ........ A61F 2/08; A61F 2/0805; A61F 2/0811; A61L 27/38; A61L 27/50; A61L 27/386

See application file for complete search history.

(56) References Cited

U.S. PATENT DOCUMENTS

2014/0067063 A1* 3/2014 Bonutti .............. A61B 17/7064 623/13.15
2018/0064544 A1* 3/2018 Grotz ...................... A61L 27/54

* cited by examiner

*Primary Examiner* — Vi X Nguyen
(74) *Attorney, Agent, or Firm* — K&L Gates LLP

(57) ABSTRACT

A method for repairing at least one of a tendon and a ligament in a joint region of a patient is provided. The method includes inserting a tube, a needle, or a combination thereof into the joint region and proximal to the at least one of a tendon and a ligament. An implantable membrane is inserted into the tube, onto the needle, or a combination thereof, in the joint region. The implantable membrane includes a biological material that promotes cell growth. The tube, the needle, or both is removed from the joint region while leaving the implantable member in the joint region and the implantable membrane contacted with the at least one of the tendon and the ligament. The method includes securing the implantable membrane in the joint region.

13 Claims, 3 Drawing Sheets

METHODS FOR ATTACHING TENDONS AND/OR LIGAMENTS TO BONE AND/OR CARTILAGE

CROSS-REFERENCE TO RELATED APPLICATIONS

This application claims priority to U.S. Provisional Patent Application No. 63/386,251, which was filed on Dec. 6, 2022, the contents of which is hereby incorporated by reference into this specification.

FIELD

The present application relates to methods for attaching tendons and/or ligaments to bone and/or cartilage.

BACKGROUND

A tendon and/or a ligament can be degraded due to injury, infection, and/or disease. The degraded tendon and/or ligament may need to be repaired by a medical procedure to remedy the injury, infection, and/or disease. There are challenges with current medical procedures to repair tendons and/or ligaments.

SUMMARY

The present disclosure provides a method for repairing at least one of a tendon and a ligament in a joint region of a patient. The method comprises inserting a tube, a needle, or a combination thereof into the joint region and proximal to the at least one of a tendon and a ligament. An implantable membrane is inserted into the tube, onto the needle, or a combination thereof, in the joint region. The implantable membrane comprises a biological material that promotes cell growth. The tube, the needle, or both is removed from the joint region while leaving the implantable member in the joint region and the implantable membrane contacted with the at least one of the tendon and the ligament. The method comprises securing the implantable membrane in the joint region.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent, and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Figure 1A:
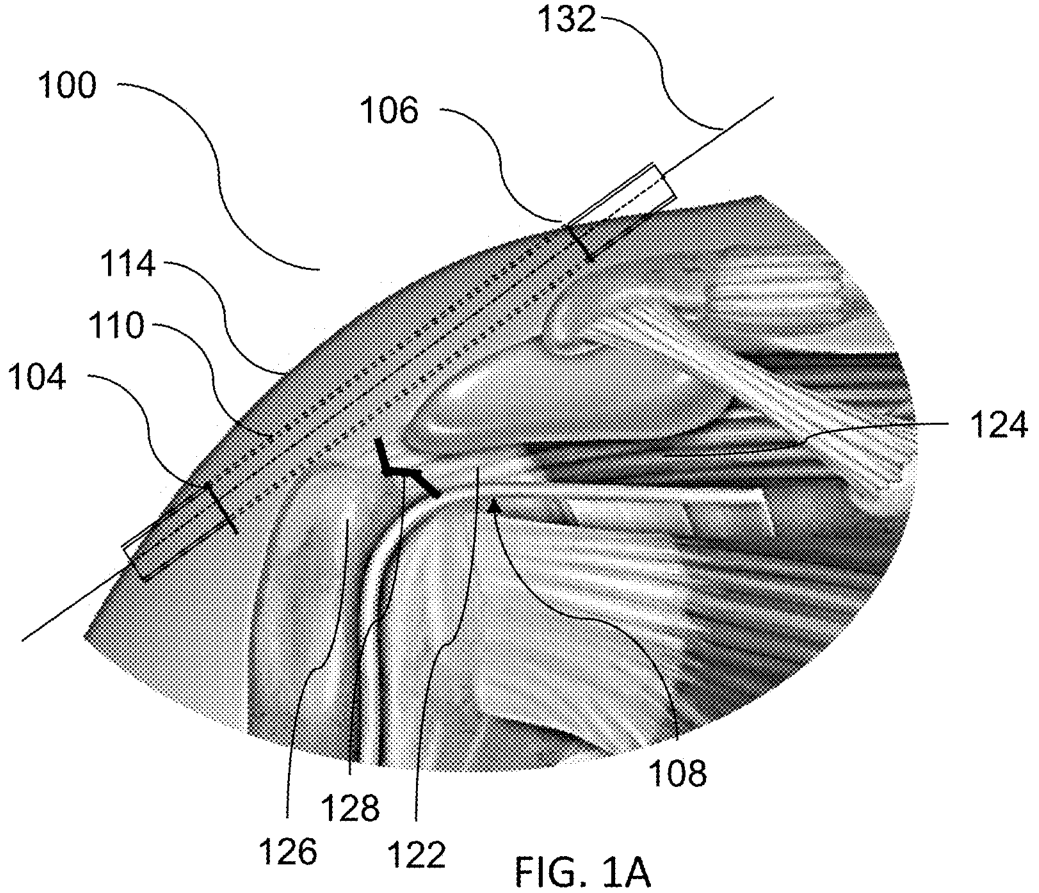
FIGS. 1A-1C illustrate schematic diagrams of various steps in a method for repairing a tendon with an implantable membrane according to the present disclosure.

Various examples of the present disclosure will now be described to provide an overall understanding of the principles of the composition, function, manufacture, and use of the compositions and methods disclosed herein. One or more examples are illustrated in the accompanying drawings. Those of ordinary skill in the art will understand that the compositions, articles, and methods specifically described herein and illustrated in the accompanying drawings are non-limiting exemplary examples and that the scope of the various examples of the present invention is defined solely by the claims. The features illustrated or described in connection with one exemplary example may be combined with the features of other examples. Such modifications and variations are intended to be included within the scope of the present invention.

A tendon can be coupled directly to a muscle and attaches the muscle to another structure such as, for example, a bone and/or cartilage. A ligament can attach non-muscle tissues, such as, for example, bones and/or cartilage, to other non-muscle tissues. A tendon and a ligament can comprise flexible and non-stretchable bundles of collagen. As used herein, the term "attachment structure" refers to a tendon, a ligament, or both a tendon and a ligament. As used herein, the term "base structure" refers to bone, cartilage, or both bone and cartilage.

An attachment structure (e.g., tendon and/or ligament) can become degraded, due to injury, infection, and/or disease as a result of, for example, a traumatic force and/or a gradual deterioration. The degradation can be a partial or complete rupture of the attachment structure. For example, a rupture of an attachment structure can be a partial or complete detachment of the attachment structure from a corresponding base structure (e.g., bone, muscle) or otherwise weakening, loosening, or disrupting, of the attachment structure at a location where the attachment structure was previously attached to the corresponding base structure. Some ruptures may require a medical procedure in order to effectively and/or efficiently repair the attachment structure as the attachment structure may only have a limited ability to repair (e.g., regenerate, regrow, reattach) on its own. For example, an attachment structure may have a lower cell density and blood supply than muscles and/or internal organs which can make the repair of the attachment structure take longer than a muscle and/or internal organ.

Thus, methods for repairing a tendon and/or ligament with an implantable membrane are provided. The methods as described in the disclosure can repair various attachment structures. The methods can repair attachment structures in a joint region, such as, for example, a shoulder joint region, a hip joint region, an elbow joint region, a knee joint region, an ankle joint region, and/or a wrist joint region. In various examples, the and methods of the present disclosure can repair the anterior cruciate ligament (ACL) in the knee joint and/or the tendon which attaches the supra-spinatus muscle (e.g., a rotator cuff tendon) to the humerus bone in the shoulder joint.

Figure 1B:
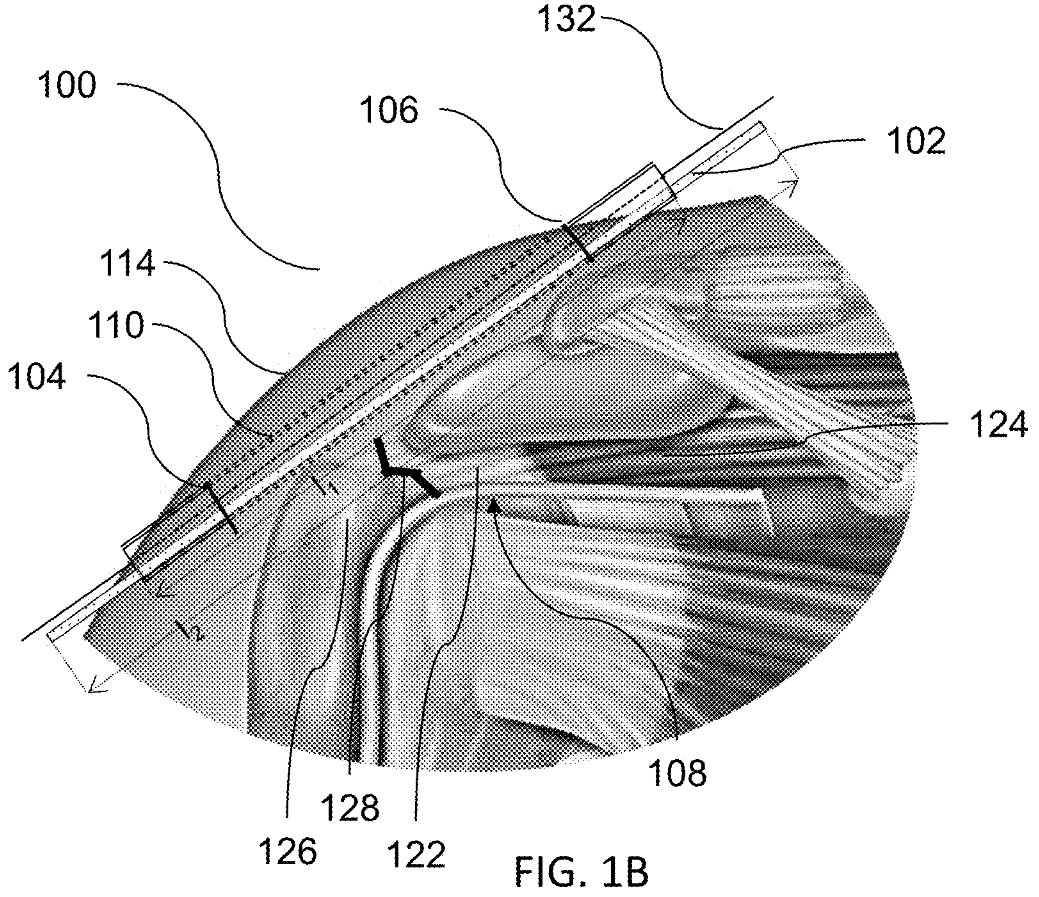
Figure 1C:
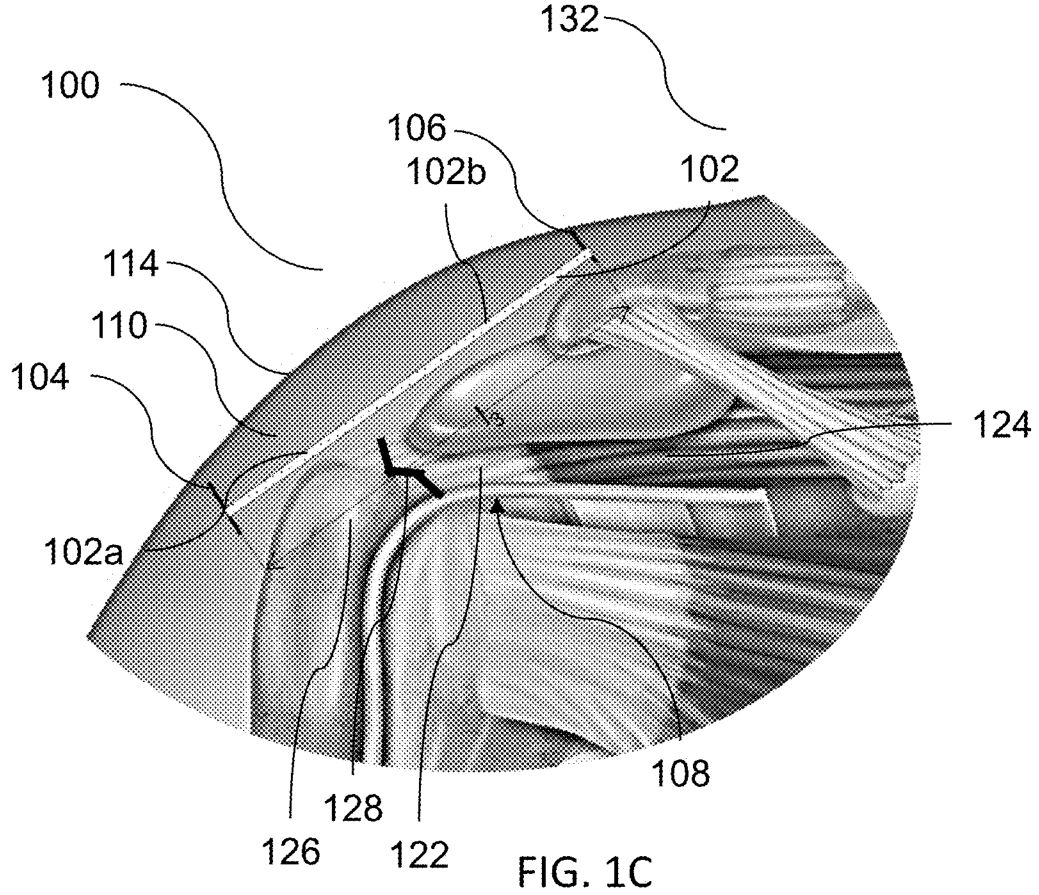

Referring to FIGS. 1A-1C, a method for repairing a tendon 122 with an implantable membrane 102 is provided. The implantable membrane 102 can be configured to repair the tendon 122 connecting the corresponding supra-spinatus muscle 124 to a humerus 126 in joint region 108 (e.g., shoulder joint region). The tendon 122 is shown having a tear (e.g., rupture) at a location 128. The repair of tendon 122 in joint region 108 is discussed herein for illustrative purposes and it is understood that the method according to the present disclosure can be applied to other tendons and/or ligaments in the shoulder joint region or other joint regions, such as, for example, the anterior cruciate ligament (ACL) in the knee joint region.

As illustrated, the tendon 122 can be prepared for surgery and optionally, the surrounding tissue in the joint region 108 can be prepared for surgery. For example, at least one of the following may occur: the surrounding tissue may be manipulated (e.g., change the position and/or orientation of the humerus 126 relative to the scapula); movement in the joint region 108 can be limited and/or the joint region 108 can be secured in a desired position; the surrounding tissue (e.g., skin) may be disinfected and/or sterilized; and anesthesia may be administered (local and/or general).

Referring to FIG. 1A, the tear in the tendon 122 at the location 128 can be imaged using various imaging techniques, such as, for example, magnetic resonance imaging (MRI). Incision 104 and incision 106 may be cut into the skin 114 proximal to the joint region 108 with a cutting tool, such as, for example, a scalpel. A guide wire 132 may be inserted into one of the incisions 104 or 106, passed through the joint region 108, and out of the other incision 104 or 106. The guide wire 132 can facilitate the insertion of the implantable membrane 102 and/or tube 110 in a desired position and/or orientation relative to the humerus 126 and the tendon 122.

In various examples, a needle may be used to puncture skin 114 and the needle may be guided through the joint region 108 and out of the skin 114. The needle may be straight, curved, angle, or the like. The needle may be used in place of the guide wire 132.

As illustrated in FIG. 1A, a tube 110 (e.g., a dilator) or other apparatus suitable to facilitate insertion of the implantable membrane 102 can be substantially aligned with and inserted over the guide wire 132, if present, and into the joint region 108 through one of the incisions 104 or 106. The tube 100 can be advanced into the joint region 108 in order to deform tissue surrounding the guide wire 132 including the tendon 122 in order to create a channel configured to receive the implantable membrane 102. The tube 110 can be passed through the joint region 108, and out of the other incision 104 or 106 such that the ends of the tube 110 are outside of the skin. In certain examples, the tube 110 is inserted between the inferior deltoid and superior deltoid and a rotator cuff tendon. The tube 110 may be inserted in either incision 104 or 106 first. In various examples, a guide wire 132 may not be used. In various examples, ultrasound, fluoroscopy, or a combination thereof may be used to guide the insertion and/or positioning of the tube 110, needle, and/or implantable membrane 102.

In various examples, a second tube (not shown) different than the tube 110 can be advanced into the joint region 108 in order to further deform the tissue surrounding the tendon 122. For example, the second tube can increase a diameter of the channel. In various examples, a balloon catheter can be advanced into the joint region 108 in order to deform tissue surrounding the tendon 122. The quantity of and/or types of devices used to create the channel may vary dependent on size of the tendon 122, size of the humerus 126, extent of the tear, and/or a desired channel size or shape.

The tube 110 can remain in the joint region 108 while another device can be inserted within the tube 110. As illustrated in FIG. 1B, the implantable membrane 102 can be inserted into the tube 110 in the joint region 108. For example, an insertion tool (e.g., graspers, clamp, rod) can introduce the implantable membrane 102 to a desired location in the joint region 108. The implantable membrane 102 can be disposed on a tip of the insertion tool and the insertion tool and implantable membrane 102 together can be advanced into the tube 110 proximal to the tendon 122. The implantable membrane 102 may comprise a length longer than the tube 110 such that the ends of the implantable membrane 102 may be exposed on either end of the tube 110 after inserting. In various examples, the insertion tool can be advanced into the tube 110 at a first end and the tip of the insertion tool can exit the tube 110 at a second end while insertion tool remains extended across a length of the tube 110. Then, the implantable membrane 102 can be disposed on a tip of the insertion tool and the insertion tool can be retracted back into the second end of the tube 100 and proximal to the tendon 122.

Upon inserting the implantable membrane 102 to the desired location, the guide wire 132 and/or needle if present and the tube 110 can be removed from the joint region 108 while leaving the implantable membrane 102 in the joint region 108 and contacting the tendon 122. For example, the tube 110 can be pulled out through either incision 104 or 106 while holding the implantable membrane 102 at the other incision 104 or 106 to inhibit the implantable membrane 102 from being pulled out with the tube 110.

In various examples, the tube 110 may not be used and the implantable membrane 102 may be inserted to the desired location with the needle. For example, the implantable membrane 102 can be attached to a second end of the needle and a first end of the needle may be punctured into the skin or introduced through either incision 104 or 106. As the needle advanced through the joint region 108, the implantable membrane 102 can be dragged into the joint region 122 and positioned proximal to the tendon 122.

A cell growth mixture can be applied onto the implantable membrane 102 and/or the tendon by, for example, a syringe. The cell growth mixture can comprise at least one of stem cells, platelets, and spun fat. The cell growth mixture can be applied before removal of the tube 110 or after removal of the tube.

The implantable membrane 102 can be cut to a desired length. For example, the implantable membrane 102 can comprise a first length, $l_1$, that is longer than a second length, $l_2$, of the tube 110 as illustrated in FIG. 1B prior to removal of the tube 110. The implantable membrane 102 can be trimmed to a third length, $l_3$, less than the first length, $l_1$, after removing the tube 110 as illustrated in FIG. 1C.

Referring to FIG. 1C, the implantable membrane 102 can be secured in the joint region 108. For example, the implantable membrane 102 can be secured in the joint region 108 by collapsing of surrounding tissue onto the implantable membrane 102 when the tube 110 is removed. In various examples, the implantable membrane 102 can be secured in the joint region 108 by securing a first portion 102*a* of the implantable membrane 102 at the incision 104, securing a second portion 102*b* of the implantable membrane 102 at the incision 106, and/or other location along the tendon 122. The implantable membrane 102 may be secured by at least one of a dowel, a staple, clotted bone marrow, clotted platelet rich plasma, an adhesive, or a combination thereof. The implantable membrane 102 can support the tendon 122 while the tendon 122 heals.

Following the method to repair the tendon 122, any remaining medical tools can be removed and incisions 104 and 106 can be closed. For example, the incisions 104 and 106 can be closed by an adhesive, a suture, or other means. The implantable membrane 102 can remain in communication with the tendon 122 and cell growth mixture can diffuse into the surrounding tissue for a period of time. The implantable membrane 102, over time, can be dissolved and/or reabsorbed by the humerus 126, the tendon 122, and/or other surrounding elements.

In various examples, a quantity of implantable membranes used to repair a degraded attachment structure can be 2 or greater implantable membranes, such as, for example, 3 or greater. The quantity of implantable membranes can change based on the application.

The methods according to the present disclosure can be for minimally-invasive surgery. As used herein, the term "surgery" refers to any type of tissue manipulation which penetrates the skin, and which involves anything more than a single type of medical device, such as, for example, a guide wire, an insertion guide, a dilator, a needle, a tamping device, and/or a trocar.

The implantable membrane 102 can be configured to repair a tendon and/or ligament. The implantable membrane 102 can be dissolved and/or reabsorbed by the joint region 108 and/or other surrounding elements. The implantable membrane 102 can comprise biological material that promotes cell growth (e.g., repair of the attachment structure), such as, for example, at least one of a placental membrane, a collagen membrane, a carbohydrate matrix, a biocompatible polymer membrane, and a biologically derived membrane. The biological material can comprise the Atreon Bti scaffold-based product available from Atreon Orthopedics Columbus, Ohio. In various examples, the biological material can promote mammalian cell growth and soft tissue repair. The implantable membrane 102 can be a scaffold.

A placental membrane can comprise interface tissues obtained from a placenta including the umbilical cord and amniotic sac. The biologically derived membrane can comprise synthetic collagenous meshes bonded to natural membranes (e.g., skin, placental membranes) by using biocompatible adhesives. For example, the biologically derived membrane can comprise at least one of the crosslinked collagen mucopolysaccharide composite material as described in U.S. Pat. No. 4,060,081 to Yannas et al., the multilayer membrane as described in U.S. Pat. No. 4,060,081 to Yannas et al., and a cell carrying collagenous membrane. In various examples, the implantable membrane 102 can comprise a placental membrane attached to a collagen membrane with a soft and pliable interface of biocompatible adhesive, such as, for example, polyacrylate, between them the placental membrane and the collagen membrane. The collagen membrane can comprise chemically crosslinked collagen fibers. The biocompatible polymer can be polyvinyl alcohol, poly acrylamide, poly acrylate, and polyethylene glycol.

The implantable membrane 102 can be formed by various processes, such as, for example, at least one of cutting, sewing, fusing, molding, pressing, and additive manufacturing. For example, in order to form the implantable membrane 102, a sheet of biological membrane can be formed in a desired shape. In certain examples, the implantable membrane 102 can be additively manufactured into the desired configuration and shape. The implantable membrane can comprise a substantially flat shape, a generally cylindrical shape, a generally elliptical shape, and/or a polygon shape. The implantable membrane 102 can be a single piece or multiple pieces. The implantable membrane 102 can comprise various levels of density, porosity, and/or permeability, as the application requires.

The cell growth mixture can promote the repair of the joint region 108, such as, for example, growth of collagen fibers within the joint region 108. The cell growth mixture can comprise at least one of stem cells, platelets, and spun fat. Stem cells can form into new and regenerated tissues and can be harvested from, for example, bone marrow. Thus, the cell growth mixture can comprise bone marrow. In various examples, the stem cells can comprise stromal precursor cells. In various examples, the cell growth mixture can comprise stromal precursor cells and spun fat as described in U.S. Patent Publication No. 2012/0156177.

The platelets can release hormones, growth factors, and/or other molecules that signal to other repair cells the location of the degradation in the attachment structure and the need to repair the degradation. The platelets can be obtained from platelet rich plasma. Thus, the cell growth mixture can comprise platelet rich plasma. In various examples, the cell growth mixture can also comprise additives, such as, for example, growth factors. In certain examples, the cell growth mixture can facilitate the formation of collagen fibers and/or facilitate deposition of collagen fibers onto the degraded attachment structure. The formation and/or deposition of the collagen fibers can facilitate repair of the degraded attachment structure.

Bone marrow can be harvested from various bones in a human and/or an animal. For example, a harvesting device, such as, for example, a trocar, can be penetrated into a bone. The trocar can penetrate through the cortex bone, the spongy bone, and into the bone marrow. A suction device (e.g., an aspirator) can be used to remove (e.g., aspirate) a desired quantity of bone marrow out of the bone through the trocar. The harvested bone marrow can be in a semi-liquefied form and can be used in the cell growth mixture. The harvested bone marrow can be from a patient that will receive the implantable membrane, a different patient, a cadaver, and/or an animal.

The dowel can comprise, for example, at least one of bone (e.g., cortex bone, spongy bone), a biocompatible polymer that can be dissolved and/or reabsorbed by a body of the subject, and a biocompatible mineral. The biocompatible polymer can comprise polyether ether ketone (e.g., PEEK). The biocompatible mineral can comprise calcium phosphate containing mineral (e.g., apatite). The biocompatible mineral can be manufactured by facilitating crystal growth of the mineral to a desired shape, sintering a powder of the mineral into a desired shape, and/or using a biocompatible glue to join a powder of the mineral together.

The dowel can be manufactured and/or harvested from various bones in a human and/or an animal, such as, for example a pelvic bone and/or a femur. The dowel can be harvested by using a harvesting device, such as, for example, a trocar in a procedure similar to how bone marrow was harvested as described above. The dowel can be harvested from a patient that will receive the implantable device, a different patient, a cadaver, and/or an animal. The dowel can be subjected to various processes to minimize the risk of immune rejection, such as, for example, removal of antigens that may provoke an immune response (e.g., chemical treatments). In various examples, the dowel can be additively manufactured. In certain examples, the dowel can comprise cortex bone from an outer portion of a pelvic bone at one end and spongy bone that was disposed intermediate the cortex bone and bone marrow at another end. The dowel can comprise a generally cylindrical shape, a generally elliptical shape, or a polygon shape. In various examples, the dowel can be dynamically trimmed to accommodate a bore formed in the base structure during a surgical procedure. The dowel can be pressed into a bore formed in a base structure for a friction fit.

Various aspects of non-limiting embodiments of inventions according to the present disclosure include, but are not limited to, the aspects listed in the following numbered clauses.

Clause 1. A method for repairing at least one of a tendon and a ligament in a joint region of a patient, the method comprising:

inserting a tube, a needle, or a combination thereof into the joint region and proximal to the at least one of a tendon and a ligament;

inserting an implantable membrane into the tube, onto the needle, or a combination thereof in the joint region, wherein the implantable membrane comprises a biological material that promotes cell growth;

removing the tube, the needle, or both from the joint region while leaving the implantable membrane in the joint region and contacting the implantable membrane with the at least one of the tendon and the ligament; and securing the implantable membrane in the joint region.

Clause 2. The method of clause 1, further comprises imaging a tear in the at least one of the tendon and ligament and cutting two incisions in skin proximal to the joint region, wherein the tube, the needle, or the combination thereof is inserted into the joint region using the two incisions.

Clause 3. The method of any of clauses 1-2, wherein insertion of the tube, the needle, or the combination thereof is guided into the joint region using ultrasound, fluoroscopy, or a combination thereof.

Clause 4. The method of any of clauses 1-3, wherein the joint region comprises a shoulder and the tube, the needle, or the combination thereof is inserted between an inferior deltoid and superior deltoid and a rotator cuff tendon.

Clause 5. The method of any of clauses 1-4, wherein at least the tube is inserted into the joint region, the implantable membrane comprise a first length that is longer than a second length of the tube, and the method further comprises trimming the implantable membrane to a third length less than the first length after removing the tube.

Clause 6. The method of any of clauses 1-5, wherein the implantable membrane is inserted into the tube in the joint region with graspers, the needle, or a combination thereof.

Clause 7. The method of any of clauses 1-6, wherein securing the implantable membrane in the joint region utilizes at least one of a dowel, a staple, clotted bone marrow, clotted platelet rich plasma, and an adhesive.

Clause 8. The method of any of clauses 1-7, further comprising cutting two incisions in skin proximal to the joint region, wherein the tube is inserted into the joint region using the two incisions and closing the incisions, after securing the implantable membrane in the joint region, using an adhesive.

Clause 9. The method of any of clauses 1-8, wherein securing the implantable membrane in the joint region comprises securing a first portion of the implantable membrane at a first incision of the two incisions, and securing a second portion of the implantable membrane at a second incision of the two incisions.

Clause 10. The method of any of clauses 1-9, wherein the at least one of the tendon and the ligament comprises a tendon which attaches a supra-spinatus muscle to a humerus.

Clause 11. The method of any of clauses 1-10, wherein the biological material comprises at least one of a placental membrane, a collagen membrane, a carbohydrate matrix, a biocompatible polymer membrane, and a biologically derived membrane.

Clause 12. The method of any of clauses 1-11, further comprising applying a cell growth mixture on the at least one of the tendon and the ligament.

Clause 13. The method of any of clauses 1-12, further comprising applying a cell growth mixture on the at least one of the tendon and the ligament, wherein the cell growth mixture comprises at least one of stem cells, platelets, and spun fat.

One skilled in the art will recognize that the herein described compositions, articles, methods, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

Reference throughout the specification to "various examples," "some examples," "one example," "an example," or the like, means that a particular feature, structure, or characteristic described in connection with the example is included in at least one example. Thus, appearances of the phrases "in various examples," "in some examples," "in one example," "in an example," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with the written description, sufficiency of description, and added matter requirements.

Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameters.

Notwithstanding that numerical ranges and parameters setting forth the broad scope of the invention are approximations, numerical values are set forth in the specific examples are reported precisely as possible. Any numerical value, however, inherently contains certain errors necessarily resulting from the standard variation found in their respective testing measurements.

The grammatical articles "a," "an," and "the," as used in this specification, including the claims, are intended to include "at least one" or "one or more" unless otherwise indicated. Thus, the articles are used in this specification to refer to one or more than one (i.e., to "at least one") of the grammatical objects of the article. By way of example, "a component" means one or more components, and thus, possibly more than one component is contemplated and can be employed or used in an implementation of the described compositions, coatings, and processes. Nevertheless, it is understood that use of the terms "at least one" or "one or more" in some instances, but not others, will not result in any interpretation where failure to use the terms limits objects of the grammatical articles "a," "an," and "the" to just one. Further, the use of a singular noun includes the plural, and the use of a plural noun includes the singular, unless the context of the usage requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various features and characteristics are described in this specification to provide an understanding of the composition, structure, production, function, and/or operation of the invention, which includes the disclosed compositions, coatings, and methods. It is understood that the various features and characteristics of the invention described in this specification can be combined in any suitable manner, regardless of whether such features and characteristics are expressly described in combination in this specification. The Inventors and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements.

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, a composition, coating, or method that "comprises," "has," "includes," or "contains" one or more features and/or characteristics possesses those one or more features and/or characteristics but is not limited to possessing only those one or more features and/or characteristics. Likewise, an element of a composition, coating, or process that "comprises," "has," "includes," or "contains" one or more features and/or characteristics possesses those one or more features and/or characteristics but is not limited to possessing only those one or more features and/or characteristics and may possess additional features and/or characteristics.

Any patent, publication, or other document identified in this specification is incorporated by reference into this specification in its entirety unless otherwise indicated but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with the written description, sufficiency of description, and added matter requirements.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A method for repairing at least one of a tendon and a ligament in a joint region of a patient, the method comprising:

inserting at least a tube into the joint region and proximal to the at least one of a tendon and a ligament;

inserting an implantable membrane into the tube in the joint region, wherein the implantable membrane comprises a biological material that promotes cell growth and a first length that is longer than a second length of the tube;

removing the tube from the joint region while leaving the implantable membrane in the joint region and contacting the implantable membrane with the at least one of the tendon and the ligament;

securing the implantable membrane in the joint region; and trimming the implantable membrane to a third length less than the first length after removing the tube.

2. The method of claim 1, further comprises imaging a tear in the at least one of the tendon and ligament and cutting two incisions in skin proximal to the joint region, wherein the tube, the needle, or the combination thereof is inserted into the joint region using the two incisions.

3. The method of claim 1, wherein insertion of the tube, the needle, or the combination thereof is guided into the joint region using ultrasound, fluoroscopy, or a combination thereof.

4. The method of claim 1, wherein the joint region comprises a shoulder and the tube, the needle, or the combination thereof is inserted between an inferior deltoid and superior deltoid and a rotator cuff tendon.

5. The method of claim 1, wherein the implantable membrane is inserted into the tube in the joint region with graspers, the needle, or a combination thereof.

6. The method of claim 1, wherein securing the implantable membrane in the joint region utilizes at least one of a dowel, a staple, clotted bone marrow, clotted platelet rich plasma, and an adhesive.

7. The method of claim 1, further comprising cutting two incisions in skin proximal to the joint region, wherein the tube is inserted into the joint region using the two incisions and closing the incisions, after securing the implantable membrane in the joint region, using an adhesive.

8. The method of claim 7, wherein securing the implantable membrane in the joint region comprises securing a first portion of the implantable membrane at a first incision of the two incisions, and securing a second portion of the implantable membrane at a second incision of the two incisions.

9. The method of claim 1, wherein the at least one of the tendon and the ligament comprises a tendon which attaches a supra-spinatus muscle to a humerus.

10. The method of claim 1, wherein the biological material comprises at least one of a placental membrane, a collagen membrane, a carbohydrate matrix, a biocompatible polymer membrane, and a biologically derived membrane.

11. The method of claim 1, further comprising applying a cell growth mixture on the at least one of the tendon and the ligament.

12. The method of claim 11, further comprising applying a cell growth mixture on the at least one of the tendon and the ligament, wherein the cell growth mixture comprises at least one of stem cells, platelets, and spun fat.

13. A method for repairing at least one of a tendon and a ligament in a joint region of a patient, the method comprising:

cutting two incisions in the skin proximal to the joint region;

inserting a tube, a needle, or a combination thereof into the joint region and proximal to the at least one of a tendon and a ligament using the two incisions;

inserting an implantable membrane into the tube, onto the needle, or a combination thereof in the joint region, wherein the implantable membrane comprises a biological material that promotes cell growth;

removing the tube, the needle, or both from the joint region while leaving the implantable membrane in the joint region and contacting the implantable membrane with at least one of the tendon and the ligament;

securing the implantable membrane in the joint region by securing a first portion of the implantable membrane at a first incision of the two incisions, and securing a second portion of the implantable membrane at a second incision of the two incisions; and after securing the implantable membrane in the joint region, closing the incisions using an adhesive.

* * * * *